United States Patent [19]
Chartrain et al.

[11] Patent Number: 5,849,568
[45] Date of Patent: Dec. 15, 1998

[54] RESOLUTION OF RACEMIC INDENE OXIDE TO YIELD (1S,2R)-INDENE OXIDE USING *DIPLODIA GOSSIPINA*

[75] Inventors: Michel M. Chartrain, Westfield; Chris H. Senanayake, North Brunswick, both of N.J.; John P. N. Rosazza, Iowa City, Iowa; Jinyou Zhang, Edison, N.J.

[73] Assignee: Merck & Co., Inc., Rahway, N.J.

[21] Appl. No.: 603,571

[22] Filed: Feb. 20, 1996

Related U.S. Application Data

[63] Continuation of Ser. No. 326,985, Oct. 21, 1994, abandoned.
[51] Int. Cl.$^6$ .............................. C12P 17/02; C12P 41/00
[52] U.S. Cl. ............................................ 435/280; 435/123
[58] Field of Search ...................................... 435/280, 123

[56] References Cited

PUBLICATIONS

Boyd, et al., "Structure and Stereochemistry of cis–Dihydro Diol and Phenol Metabolites of Bicyclic Azaarenes . . . ", J. Chem. Soc., Perkin Trans., pp. 1065–1071, 1993.

Chien, et al., "Microbial Transformations of Natural Antitumour Agents.", J. Chem. Soc., Perkin Trans., pp. 1352–1356, 1981.

Pedragosa–Moreau et al., "Microbial Transformations. 28. Enantiocomplementary Epoxide Hydrolyses . . . ", J. Org. Chem., 58, pp. 5533–5536, 1993.

Sutherland, et al., "Enantiomeric Composition of the trans-–Dihydrodiols Produced from Phenanthrene by Fungi", Applied & Environ. Microb., vol. 59, No. 7, pp. 2145–2149, Jul. 1993.

Yamada, et al., "Microbial Transformation of (+)–Epoxyaurapten by *Pseudomonas aeruginosa*", Biosci. Biotech. Biochem., 56 (1), pp. 153–154, 1992.

Holland HL, Biocatalysis 10:65–76 (1994).

*Primary Examiner*—Sandra E. Saucier
*Attorney, Agent, or Firm*—Kenneth R. Walton; Melvin Winokur

[57] ABSTRACT

A process is disclosed that hydrolyzes, by the action of an epoxide hydrolase of *Diplodia gossipina* (alternatively named *Diplodia gossypina*) ATCC 16391 or ATCC 10936, the undesired enantiomer of racemic indene oxide, an epoxide of indan.

5 Claims, No Drawings

RESOLUTION OF RACEMIC INDENE OXIDE TO YIELD (1S,2R)-INDENE OXIDE USING *DIPLODIA GOSSIPINA*

This application is a continuation of U.S. Ser. No. 08/326,985, filed Oct. 21, 1994, abandoned.

BACKGROUND OF THE INVENTION

The present application is related to Merck 18996, U.S. Ser. No. 08/059,038, filed May 7, 1993, and 18996IA.

The present invention is concerned with a process for synthesizing intermediates for compounds which inhibit the protease encoded by human immunodeficiency virus (HIV), and in particular certain oligopeptide analogs, such as Compounds J and K in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns a bioresolution of racemic epoxides, as illustrated by the following scheme.

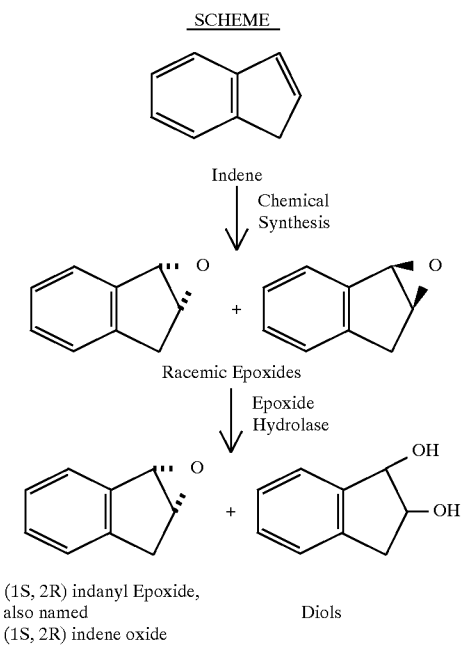

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.,* 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature,* 313, 277 (1985)]. Amino acid sequence homology provides evidence that the pol sequence encodes reverse transcriptase, an endonuclease and an HIV protease [Toh, H. et al., *EMBO J.,* 4, 1267 (1985); Power, M. D. et al., *Science,* 231, 1567 (1986); Pearl, L. H. et al., *Nature,* 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein, also illustrated in the Examples below.

The present application discloses an improved process to make, in substantial enantiomeric purity, 1(S)-amino-2(R)-hydroxy indanyl side chain of the structure

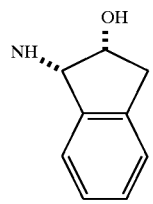

which is a sidechain group of Compound J and K, both of which are potent inhibitors of HIV protease.

Previous attempts at synthesis involve inefficient production of the racemate 1(±)-amino-2(±) hydroxy indan from the racemic indene oxide. Applicants have provided a method of hydrolyzing the undesired (1R,2S) indene oxide, of the structure

by incubation of the racemic indene oxide with a cell suspension of *Diplodia gossipina* ATCC 16391 or ATCC 10936 to give the optically pure (1S,2R) enantiomer.

BRIEF DESCRIPTION OF THE INVENTION

The present invention provides new methods to effect the synthesis of 1(S)-amino-2(R)-hydroxy indane, by bioconversion. The product compounds are intermediates for compounds useful in the synthesis of inhibitors of HIV protease, renin and other proteases, e.g. Compounds J and K.

DETAILED DESCRIPTION OF THE INVENTION

The present invention is concerned with a process for synthesizing intermediates for compounds which inhibit the HIV protease. The desired intermediate is (1S,2R) indanyl epoxide substantially free of its undesired enantiomer (1R, 2S) indanyl epoxide.

In this invention, a process is described for synthesizing (1S,2R) indanyl epoxide in substantially 100% enantiomeric excess from a mixture of enantiomers of (1R,2S) indanyl epoxide and (1S,2R) indanyl epoxide, comprising the steps of (a) providing a quantity of a mixture of enantiomers of (1R,2S) indanyl epoxide and (1S,2R) indanyl epoxide in buffer;

(b) incubating the mixture with a suspension of fungal cells having epoxide hydrolase, until substantially all of (1R,2S) indanyl epoxide is consumed; and (c) isolating the resulting (1S,2R) indanyl epoxide.

In one embodiment, the process of this invention is limited to fungal cells which are *Diplodia gossipina* or *Lasiodiplodia theobromae*.

In another embodiment, the process of this invention is further limited to *Diplodia gossipina* derived from ATCC 16391 or from ATCC 10936.

In another embodiment, the process of this invention is conducted in buffer of about 0.1M Tris, pH about 7.5, containing about 10% acetonitrile.

In another embodiment, the process of this invention is a process of synthesizing (1S,2R) indanyl epoxide in substantially 100% enantiomeric excess from a mixture of enantiomers of (1R,2S) indanyl epoxide and (1S,2R) indanyl epoxide, comprising the steps of (a) providing a quantity of a mixture of enantiomers of (1R,2S) indanyl epoxide and (1S,2R) indanyl epoxide, at a concentration of about 1 g/L of said mixture in about 0.1M Tris, pH about 7.5, containing about 10% acetonitrile;

(b) incubating the mixture with a suspension of fungal cells derived from *Diplodia gossipina* ATCC 16391 or ATCC 10936, until substantially all of (1R,2S) indanyl epoxide is consumed; and (c) isolating the resulting (1S,2R) indanyl epoxide.

Applicants have discovered that the buffer system needed optimizing to stabilize the epoxide substrates, as well as retain enzymatic activity of this epoxide hydrolase. The most suitable buffer system is about 0.1M Tris, pH about 7.5, in about 10% acetonitrile. Other suitable buffer systems are readily available and are readily determined by the skilled artisan.

The preferred bioconverting microorganism is *Diplodia gossipina* (also known as *Diplodia gossypina*), deposited at the American Type Culture Collection (ATCC 16391). Other suitable fungal microorganisms include, but are not limited to, *Lasiodiplodia theobromae* MF 5215 (ATCC 10936), which has been classified as *Diplodia gossipina* and is closely similar to ATCC 16391.

ATCC Deposit 16391

Before the U.S. filing date of the present application, a sample of the microorganism *Diplodia gossipina* had been deposited at the American Type Culture Collection (ATCC), 10801 University Blvd. Manassas, Va. 20110. The culture access designation is 16391. Application for conversion to a Budapest Treaty deposit was applied for on or about 15 Oct. 1994. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

ATCC Deposit 10936

Before the U.S. filing date of the present application, a sample of the microorganism *Diplodia gossipina* had been deposited at the American Type Culture Collection (ATCC), 10801 University Blvd. Manassas, Va. 20110. The culture access designation is 10936. Application for conversion to a Budapest Treaty deposit was applied for on or about 15 Oct. 1994. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics of ATCC 16391 and ATCC 19036

The physical characteristics and taxonomy, including morphological, cultural, biological and physiological characteristics are briefly described hereinbelow. The general characteristics of ATCC 16391 and 10936 are the same, except when noted.

On the basis of the taxonomic analysis performed thus far, both microorganisms have been assigned to the order *Diplodia gossypina*, also known as *Diplodia gossipina*. See Jones, J. P., *Mycotaxon* 6, 24–26 (1977) and *CMI Description of Pathogenic Fungi and Bacteria* No. 519 (3 pages). (Commonwealth Agricultural Bureaux, 1976).

Each culture grows well on routine media including trypticase soy agar (28° and 37° C.), yeast malt extract agar, glycerol asparagine agar, inorganic salt starch agar, oatmeal agar, Czapek Dox, Czapek solution agar and peptone agar, and Bennett's agar, all at 28° C.

Colonies on oat agar are greyish sepia to mouse grey to black, fluffy with abundant serial mycelium; reverse fuscous black to black Pycnidia simple, or compound, often aggregated, stromatic, ostiolate, frequently setose, up to 5 mm wide. Conidiophores are hyaline, simple, sometimes septate, rarely branched cylindrical, arising from the inner layers of cells lining pycnidial cavity. Conidiogenous cells are hyaline simple, cylindrical to subobpyriform, holoblastic annelidic. Conidia are initially unicellular, hyaline, granulose, subovoid to ellipsoide-ooblong, thick-walled, base truncate; mature Conidia are uniseptate, cinnamon to fawn, often longitudinally striate, (18-) 20–30×10–15 $\mu$. Paraphyses when present are hyaline cylindrical, sometimes septate, up to 50$\mu$ long.

Pycnidia on leaves, stems and fruits are immersed, later becoming erumpent, simple or grouped, 2–4 mm wide, ostiolate, frequently pilose with Conidia extruding in a black mass.

HOSTS: Plurivorous, on approximately 500 host plants. Also isolated from ulcerated human cornea, lesions, on nail and subcutaneous tissue.

DISEASES: Causing or associated with damping-off, wilt, blight, dieback root rot, collar rot, stem necrosis, panel necrosis of rubber, gummosis, black band diseases of jute, stump rot, bole rot, rot of sugarcane, leaf spot, witches' broom, fruit blights, fruit rot, pod rot of cacao, boll rot of cotton, seed rot, storage rot cassava, sweet potato and yams. Also causes loss of cuttings in cacao and budding failure in rubber. Blue staining of timber and blue spotting crepe rubber.

GEOGRAPHICAL DISTRIBUTION: World-wide but mainly confined to an area 40° north to 40° south of the equator.

PHYSIOLOGIC SPECIALIZATION: An unspecialized virulent rot pathogen. An isolate from one host is capable of infecting different hosts. Several races, distinguishable in culture, are known to exist.

In general, ATCC 16391 strain or ATCC 10936 strain are cultured in an aqueous nutrient medium containing sources of assimilable carbon and nitrogen, preferably under submerged aerobic conditions (e.g., shaking culture, submerged culture, etc.). The aqueous medium is preferably maintained at a pH of about 5.5 at the initiation and termination (harvest) of the fermentation process. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred source of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions are preferred. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 5.5 prior to the autoclaving step.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 64 hours, which may be varied according to fermentation conditions and scales. Preferably, the production cultures are incubated for about 48 hours at 28° C. on a rotary shaker operating at 220 rpm.

Preferred culturing/production media for carrying out the fermentation include the following media:

|  | g/L |
|---|---|
| YME |  |
| Malt Extract | 20 |
| Yeast Extract | 3 |
| Glucose | 3 |

-continued

|  | g/L |
|---|---|
| CFM |  |
| Potato Dextrose Broth | 24 |
| Yeast Extract | 3 |
| CFM microelement solution | 1 ml |
| MOPS buffer, and sodium hydroxide to bring pH up to 7.0 | 20 |
| Microelement solution contains: |  |
| $KH_2PO_4$, | 0.8 |
| $CuSO_4.5H_2O$ | 0.64 |
| $FeSO_4.7H_2O$ | 0.11 |
| $MnCl_2.4H_2O$ | 0.8 |
| $ZnSO_4.7H_2O$ | 0.15 |

Note the addition of 10% acetonitrile to enhance stability of epoxide substrates. Alternatively 5–15% EtOH may be used instead of acetonitrile, or a mixture thereto. There are other stability enhancers, including 10–15% THF, or any alcoholic solvent at about 5–15%. Alternative buffers include phosphates.

After growth is completed, the cells are harvested by conventional methods, e.g., centrifugation and filtration, and then washed and resuspended in the appropriate buffer.

The product (1S,2R) indene oxide can be recovered from the culture medium by conventional means which are commonly used for the recovery of other known substances. The substances produced are found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is solvent extraction, particularly using methylene chloride.

FORMULATIONS

The product compounds synthesized from the intermediates of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds, including their use as controls. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,168. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,168 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention. A mixture of enantiomers includes a 1:1 mixture, as well as any other mixture, e.g., 1:4, 4:3, 2:1.

Representative experimental procedures utilizing the novel process are detailed below. These procedures are exemplary only and are not limitations on the novel process of this invention.

EXAMPLE 1

A. Chemicals and Media

KF medium was used as the seed medium and YME as the production medium. The compositions of all the media used are listed in Table 1. Tris buffer [Tris (hydroxymethyl) aminomethane] was used for the bioconversion.

B. Seed Stage

A loopful of cells taken from a YME/agar slant was inoculated to a 250-ml Erlenmeyer flask containing 50 ml of seed medium. The culture was aerobically incubated on an rotary shaker (220 rpm) for 48 hours at 28° C.

C. Production Stage

A baffled 250-ml Erlenmeyer flask containing 50 ml of production medium was inoculated with 3 ml of seed culture. The culture was aerobically incubated on a rotary shaker (220 rpm) for 48 hours at 28° C.

D. Screening Methods

Fungal cultures were cultivated under the conditions described above. The cells were harvested by centrifugation and washed twice with 0.1M Tris buffer at a pH of 7.5. The cells were further washed once with 0.1M Tris/pH 7.5 containing 10% acetonitrile before resuspending in the same buffer/solvent system, at a packed cell volume to buffer/solvent ration of 1.5:1. One g/L of racemic epoxides (dissolved in acetonitrile) was added to the cell suspension to initiate the biotransformation. The reaction was carried out at ambient temperature on an oscillatory shaker, monitored by sampling at regular intervals. The samples were divided, with one portion extracted by heptane for enantiometric excess (ee) analysis, and the other portion diluted directly for epoxide concentration measurement.

E. Reverse Phase Assay

To determine the concentration of the epoxides in samples, a reverse phase HPLC column (4.6 mm×25 cm), a UV detector, and two pumps equipped for solvent delivery were used. The epoxide concentration was analyzed by an isocratic method employing a mobile phase comprised of 60% (v/v) of 0.01M potassium phosphate/pH 7.5 and 40% (v/v) acetonitrile, at a flow rate of 1.0 ml/ minute. The detection was by UV absorbance at 220 nm. The two epoxide enantiomers (1S,2R and 1R,2S) showed up as a single peak on the chromatogram, hence only allowing measurement of total epoxides in the sample.

F. Epoxide Chiral Assay

This assay employed a normal phase column which gave good separation between the 1S,2R and 1R,2S enantiomers. The column (4.6 mm×25 cm), an HPLC equipped with an autosampler, a UV detector, and two pumps for solvent delivery were used for HPLC analysis via a computer-controlled program. The mobile phase was comprised of 97% hexane and 3% isopropanol at a flowrate of 1.0 ml/minute. The eluate was monitored at 230 nm.

EXAMPLE 2

Culture Screening

Based on literature (*J. Org. Chem.*, 58, 5533–5536, (1993)), fungal strains were chosen to screen for the desired enzyme. Eighty cultures were examined, and 10% of them were found to preferentially hydrolyze the undesired 1R,2S epoxide thus enriching the 1S,2R enantiomer (Table 1). *Diplodia gossipina* ATCC 16391 and *Lasiodiplodia theobromae* MF 5215 showed the strongest activities of the epoxide hydrolase, and yielded 100% enantiometric excess during a four-hour reaction.

TABLE 1

Cultures Capable Of Bioresolving Racemic Epoxides

| CULTURE NAME | EE % (1S,2R)* |
|---|---|
| *Diplodia gossipina* ATCC 16391 | 100 |
| *Lasiodiplodia theobromae* MF 5215 (ATCC 10936) | 100 |
| *Aspergillus niger* MF 1667 | 71 |
| *Aspergillus caespitosur* MF 1664 | 70 |
| *Aspergillus niger* MF 1909 | 61 |
| *Mortierella isabellina* MF 5223 | 49 |
| *Mortierella isabellina* MF 5222 | 45 |
| *Scopolariopsis* sp. GB 3329 | 42 |

*Each culture was grown in YME medium for 2, 4 and 6 days before harvesting, and the maximum ee values from a 4-hour reaction are listed.

EXAMPLE 3

Effect of Culture Age on Bioresolution of Epoxides

Culture age did not appear to affect the bioresolution activity of ATCC 16391, as the cells harvested from 2 to 9 days were all capable of totally resolving racemic epoxides after 4-hour reaction. However, culture age had an effect on bioresolution by several other cultures as shown in Table 2. For *Aspergillus niger* MF 1909, the 2-day culture demonstrated the highest enzymatic activity with a steady decrease for the older cultures; *Aspergillus caespitosur* MF 1664 had the highest enzymatic activity after 4 days of growth. The activity of MF 1667 heavily depended on culture age, and the highest ee% could only be achieved by 4–5 day old cells.

TABLE 2

Effect Of Culture Age On Bioresolution Of Racemic Epoxides

| CULTURE NAME | EE % (1S,2R)* 2-day | EE % (1S,2R)* 4-day | EE % (1S,2R)* 6-day |
|---|---|---|---|
| *Diplodia gossipina* ATCC 16391 | 100 | 100 | 100 |
| *Lasiodiplodia theobromae* MF 5215 | 97 | 99 | 100 |
| *Aspergillus niger* MF 1667 | 54 | 71 | 35 |
| *Aspergillus caespitosur* MF 1664 | 42 | 70 | 50 |
| *Aspergillus niger* MF 1909 | 61 | 21 | 17 |
| *Mortierella isabellina* MF 5223 | 39 | 39 | 50 |
| *Mortierella isabellina* MF 5222 | 45 | 35 | 36 |
| *Scopolariopsis* sp. GB 3329 | 42 | 31 | 24 |

*Culture were grown in YME medium for 2, 4 and 6 days before harvesting, and the ee values from 4-hour reactions are listed.

EXAMPLE 4

Effect of Culture Medium on Bioresolution of Epoxides

Six different culture media were tested using ATCC 16391, namely: Minimal, Peptone, KF, CSL, CFM, and YME (Table 3). The poorest bioconversion was obtained in the minimal medium, and the best from YME and CFM.

TABLE 3

MEDIUM COMPOSITIONS

| | g/L |
|---|---|
| YME | |
| Malt Extract | 20 |
| Yeast Extract | 3 |
| Glucose | 3 |
| KF | |
| Corn Steep Liquor | 5 |
| Tomato Paste | 40 |
| Oatmeal Flour | 10 |
| Glucose | 10 |
| KF trace element solution and sodium hydroxide to pH 6.8 | 10 ml |
| Trace element solution: | |
| $FeSO_4 \cdot 7H_2O$ | 1 |
| $MnSO_4 \cdot 4H_2O$ | 1 |
| $CuCl_2 \cdot 2H_2O$ | 0.025 |
| $CaCl_2$, 0.056 | 0.1 |
| $H_3BO_3$ | 0.056 |
| $(NH_4)_6Mo_7O_{24} \cdot 4H_2O$ | 0.019 |
| $ZnSO_4 \cdot 7H_2O$ | 0.2 |
| CFM | |
| Potato Dextrose Broth | 24 |
| Yeast Extract | 3 |
| Microelement solution | 1 ml |
| MOPS buffer, and sodium hydroxide to bring pH to 7.0 | 20 |
| Microelement solution: | |
| $KH_2PO_4$ | 0.8 |
| $CuSO_4 \cdot 5H_2O$ | 0.64 |
| $FeSO_4 \cdot 7H_2O$ | 0.11 |
| $MnCl_2 \cdot 4H_2O$ | 0.8 |
| $ZnSO_4 \cdot 7H_2O$ | 0.15 |
| Minimal | |
| $KH_2PO_4$ | 5 |
| $MgSO_4 \cdot 7H_2O$ | 2.5 |
| Sucrose | 50 |
| $KNO_3$ | 10 |
| $FeCl_3$ | 0.02 |
| Peptone Dextrose | |
| glucose | 40 |
| peptone | 10 |
| CSL | |
| corn steep liquor | 10 |
| glucose | 50 |
| $MgSO_4 \cdot 7H_2O$ | 2 |

EXAMPLE 5

Preparation of N-(2(R)-hydroxy-1(S)-indanyl)-2(R)-phenylmethyl-4(S)-hydroxy-5-(1-(4-(3-furo[2,3-b]-pyridylmethyl)-2(S)-N'-(t-butylcarboxamido)piperazinyl))-pentaneamide

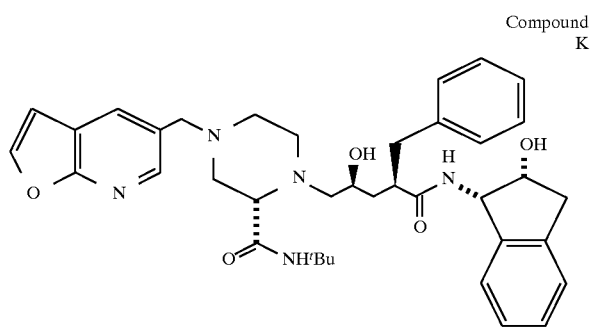

Compound K

To a solution of N-(2(R)-hydroxy-1(S)-indanyl)-2(R)-phenylmethyl-4(S)-hydroxy-5(-2(S)-N'-(t-butylcarboxamido)piperazinyl))pentaneamide (6.50 g, 12.48 mmol) dissolved in 12 mL of dimethylformamide, under argon, was added 3-chloromethylfuro-[2,3-b]pyridine hydrochloride (2.80 g, 13.72 mmol) and triethylamine (5.21 mL, 37.44 mmol). After 18 h the reaction mixture was diluted with 400 mL of ethyl acetate and washed with sat'd $NaHCO_3$ (1×25 mL), water (5×20 mL), and brine (1×25 mL). The solution was dried over $MgSO_4$, filtered and concentrated to an oil. The residue was purified via flash column chromatography (60×150 mm column, gradient elution $CH_2Cl_2$:$CH_2Cl_2$ sat'd with $NH_3$: MeOH 60:39:1.0 (1000 mL), 60:38:2 (1500 mL), 60:37:3 (1500 mL), 60:36:4 (1500 mL). Titrated the resulting foam in ethyl acetate and the desired product was filtered and dried overnight under high vacuum at 65° C. to provide 5.30 g of white crystalline solid. Mixed fractions from the column chromatography could be combined and repurified to afford more product. m.p. 183.5°–184.5° C.

$^1$H NMR (400 MHz, $CDCl_3$) δ8.25 (d, J=2.2 Hz, 1H), 7.85 (d, J=2.0 Hz, 1H), 7.75 (s, 1H), 7.73 (d, J=2.4 Hz, 1H), 7.32–7.10 (m, 9H), 6.75 (d, J=2.4 Hz, 1H), 5.95 (d, J=8.6 Hz, 1H), 5.27 (dd, J=8.5, and 4.8 Hz, 1H), 4.27–4.26 (m, 1H), 4.12 (br s, 1H), 3.89–3.83 (m, 1H), 3.51 (s, 2H), 3.29 (dd, J=17.5 and 4.0 Hz, 1H), 3.16 (dd, J=3.66 and 3.48 Hz, 1H), 3.15 (dd, J=6.6 and 5.1 Hz, 1H), 2.94–2.50 (m, 11H), 2.36–2.34 (m, 1H), 1.66 (s, 1H), 1.62–1.47 (m, 1H), 1.35 (s, 9H).

Analysis calculated for $C_{38}H_{47}N_5O_5$ C, 69.81; H, 7.25; N, 10.71. Found: C, 69.46; H, 7.22; N, 10.69.

EXAMPLE 6
A. Preparation of Furo[2,3-b]pyridine-5-carboxylic acid

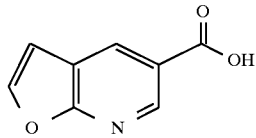

To a suspension of furo[2,3-b]pyridine-2,5-dicarboxylic acid (0.36 g, 1.484 mmol) in 3 mL of quinoline, under Ar, was added Cu powder (180 mg, 2.82 mmol) and warmed to 210 C. for 1.5 h. The reaction was cooled to RT and diluted with 50 mL of methylene chloride and filtered through celite. The organic layer was extracted with sat'd $NaCO_3$ (2×40 mL), acidified to pH 3 with 3N HCl, and filtered to afford 80 mg of a tan solid. The aqueous layer was extracted with ether/methanol (85/15) (3×50 mL) and washed with brine (1×10 mL), dried over $MgSO_4$, filtered and concentrated to afford an additional 35 mg of product. $^1$H NMR (400 MHz, $CD_3OD$) δ8.89 (s, 1H), 8.67 (d, J=2.0 Hz, 1H), 7.97 (d, J=2.5 Hz, 1H), 7.01 (d, J=2.4 Hz, 1H).

B. Preparation of methyl furo[2,3-b]pyridine-5-carboxylate

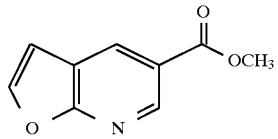

To furo[2,3-b]pyridine-5-carboxylic acid (3.0 g, 18.40 mmol) dissolved in 40 mL of methanol was added 160 mL of chloroform and then trimethysilyldiazomethane (42 mL, 10% solution in hexanes) slowly. After 0.5 h 4 drops glacial acetic acid was added and the reaction mixture was concentrated. This provided 3.20 g as an off white solid. $^1$H NMR (400 MHz, $CDCl_3$) δ9.02 (d, J=2.0 Hz, 1H), 8.60 (d, J=2.0 Hz, 1H), 7.79 (d, J=2.5 Hz, 1H), 6.87 (d, J=2.5 Hz, 1H), 3.98 (s, 3H).

C. Preparation of 5-hydroxymethyl furo[2,3-b]pyridine

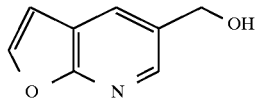

A flame dried 500 mL round bottom flask was charged with methyl furo[2,3-b]pyridine-5-carboxylate (3.20 g, 18.08 mmol) dissolved in 90 mL of THF and cooled to 0° C. To this was added diisobutylaluminum hydride (46 mL, 46.1 mmol, 1M solution in hexanes) over 10 minutes and the cooling bath removed. After 4 h the reaction mixture was cooled to 0° C. and slowly quenched with rochelle salts (100 mL). After an additional 18 h the layers were separated and the aqueous layer was extracted with ethyl acetate (4×40 mL). The combined organic layers were washed with brine (1×20 mL), dried over $MgSO_4$, filtered and concentrated. The residue was purified via flash column chromatography (40×150 mm column, gradient elution $CH_2Cl_2$:$CH_2Cl_2$ sat'd with $NH_3$: MeOH 60:39:1.0 (1000 mL), 60:38:2 (1000 mL), 60:37:3 (1000 mL), 60:36:4 (1000 mL). This provided 2.16 g of a white solid. $^1$H NMR (400 MHz, $CDCl_3$) δ8.19 (d, J=2.0 Hz, 1H), 7.92 (d, J=2.0 Hz, 1H), 7.64 (d, J=2.5 Hz, 1H). 6.69 (d, J=2.4 Hz, 1H), 4.78 (d, J=3.8 Hz, 2H), 4.69 (br s, 1H).

D. Preparation of 3-chloromethyl furo[2,3-b]pyridine-hydrochloride

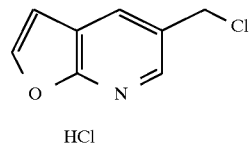

To a solution of 5-hydroxymethyl furo[2,3-b]pyridine dissolved in 9 mL of methylene chloride cooled to 0° C. was added thionyl chloride (4.23 mL, 57.99 mmol). The ice bath was removed and after 1 h the reaction mixture was concentrated to afford 2.86 g of an off white solid. $^1$H NMR (400 MHz, $CDCl_3$) δ8.40 (d, J=2.0 Hz, 1H), 8.13 (d, J=2.2 Hz, 1H), 7.80 (d, J=2.4 Hz, 1H), 6.86 (d, J=2.4 Hz, 1H), 4.74 (s, 2H).

EXAMPLE 7
Preparation of Amide 9

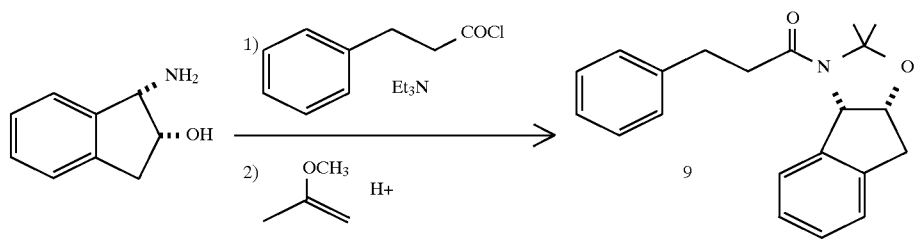

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

retention time (min) identity 6.3 cis-aminoindanol

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous NaHCO$_3$ (10 L). The mixture was agitated and the layers were separated. The ethyl acetate extract was washed with 5% aqueous NaHCO$_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 9 (86.4%, 98 area % by HPLC). $^1$H NMR (300.13 MHz, CDCl$_3$, major rotamer) δ8 7.36–7.14 (m, 9H), 5.03 (d, J=4.4, 1H), 4.66 (m, 1H), 3.15 (m, 2H), 3.06 (br s, 2H), 2.97 (m, 2H), 1.62 (s, 3H), 1.37 (s, 3H); $^{13}$C NMR (75.5 MHz, CDCl$_3$, major rotamer) δ$_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

Analysis calculated for C$_{21}$H$_{23}$NO$_2$: C, 78.47; H, 7.21; N, 4.36. Found: C, 78.65; H, 7.24; N, 4.40.

EXAMPLE 8
Preparation of Epoxide 11 Tosylate Method

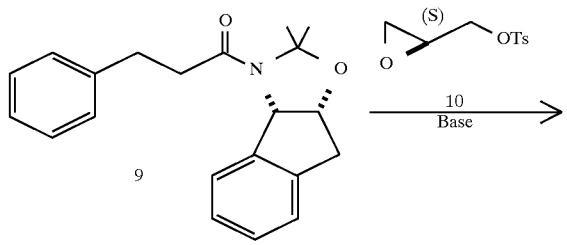

A solution of acetonide 9 (1000 g, 3.11 mol) and 2(S)-glycidyl tosylate 10 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide (LiN[(CH$_3$)$_3$Si]$_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min) | identity |
|---|---|
| 5.5 | amide 9 |
| 6.5 | glycidyl tosylate 10 |
| 13.5 | epoxide 11 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 11 (61.2%, 98.7 area % of the major epoxide by HPLC). $^{13}$C NMR (300 MHz, CDCl$_3$) δ171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 9
Preparation of penultimate 14

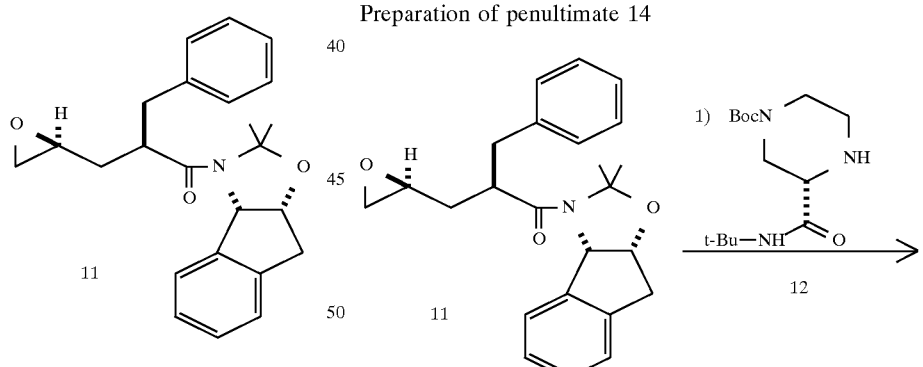

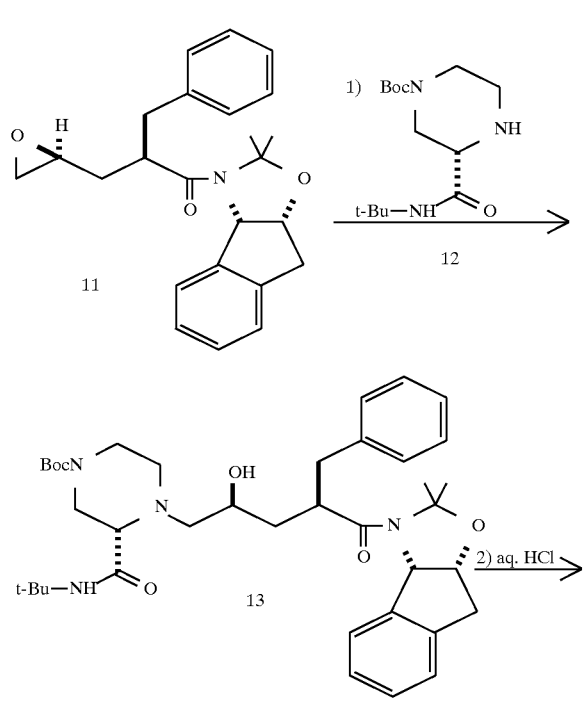

-continued

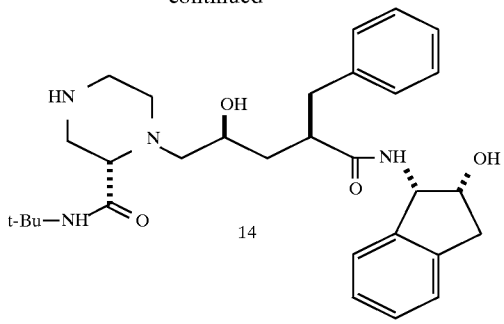

A slurry of the 2(S)-t-butylcarboxamide-4-N-Boc-piperazine 12 (1950 g, 6.83 mol, >99.5% ee) (ee= enantiomeric excess) and the epoxide 11 (2456 g, 97.5:2.5 mixture of 4 S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM ($KH_2PO_4/K_2HPO_4$), 1.0 mL/min., detection=220 nm, sample preparation=2 μL, reaction mixture diluted to 1 mL in acetonitrile. Approximate retention times:

| retention time (min) | identity |
|---|---|
| 4.8 | piperazine 12 |
| 8.9 | epoxide 11 |
| 15.2 | coupled product 13 |

After 28 h, the remaining epoxide 11 and coupled product 13 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 14 |
| 15.1 | coupled product 13 |

The mixture was cooled to 0° and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 14 in ethyl acetate was 86.5%. The penultimate compound 14 in DMF was directly used in the next step without further purification. For isolated 14: $^{13}C$ NMR (75.4 MHz, $CDCl_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 10

Preparation of monohydrate of Compound J

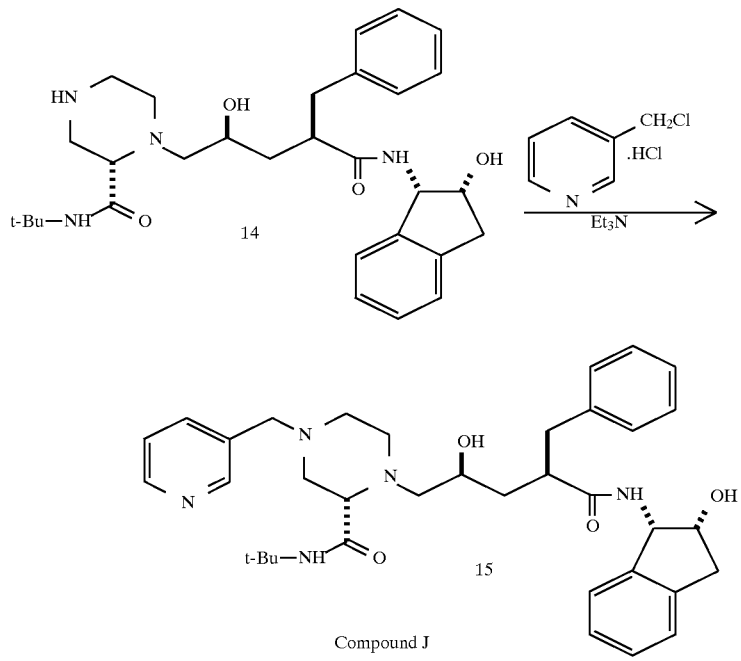

Compound J

The solution of 14 in DMF (10.5 L, KF=10 mg/mL) from the previous step was charged with 8 L of sieve dried DMF (KF. <30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 14 |

The mixture was aged at 68° C. until the residual penultimate compound 14 was <0.3 area % by HPLC analysis.

The mixture was stirred at 68° C. for 4 h, then cooled to 25° C. and partitioned with ethyl acetate (80 L) and a mixture of 24 L of saturated aqueous $NaHCO_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 11
Pyrazine-2-tert-butyl carboxamide 17

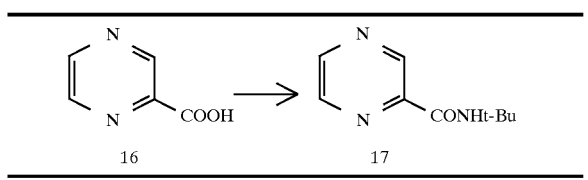

| 2-Pyrazinecarboxylic acid (8) | 3.35 kg (27 mol) |
|---|---|
| Oxalyl chloride | 3.46 kg (27.2 mol) |
| tert-Butylamine (KF = 460 μg/ml) | 9.36 L (89) |
| EtOAc (KF = 56 μg/ml) | 27 L |
| DMF | 120 mL |
| 1-Propanol | 30 L |

The carboxylic acid 16 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 16 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 16=10.7 min, amide 17=28.1 min.

The reaction mixture was aged at 5° C. for 1 h. The resulting slurry was cooled to 0° and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 17 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atmospheric pressure for several days. Evaporation of an aliquot gave a tan solid m.p. 87°–88° C. $^{13}C$ NMR (75 MHz, $CDCl_3$, ppm) 161.8, 146.8, 145.0, 143.8, 142.1, 51.0, 28.5.

EXAMPLE 12
rac-2-tert-Butyl-carboxamide-piperazine 18

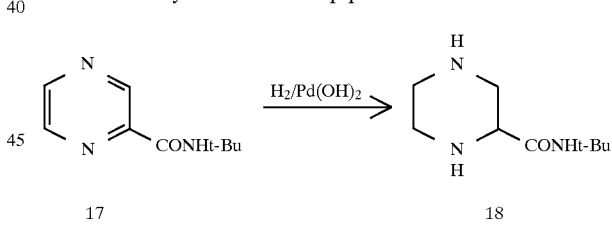

Materials

Pyrazine-2-tert-butylcarboxamide 17 2.4 kg (13.4 mol) in 1-Propanol solution 12 L 20% $Pd(OH)_2/C$ 16 wt. % water 144 g.

The pyrazine-2-tert-butylcarboxamide 17/1-propanol solution was placed into the 5 gal autoclave. The catalyst was added and the mixture was hydrogenated at 65° C. at 40 psi (3 atm) of $H_2$.

After 24 h the reaction had taken up the theoretical amount of hydrogen and GC indicated <1% of 17. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 17=7.0 min, 18=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 18 is 133 g/L.

Evaporation of an aliquot gave 18 as a white solid m.p. 150°–151° C.; $^{13}$C NMR (75 MHz, $D_2O$, ppm) 173.5, 59.8, 52.0, 48.7, 45.0, 44.8, 28.7.

EXAMPLE 13
(S)-2-tert-Butyl-carboxamide-piperazine bis (S)-Camphorsulfonic acid salt (S)-19

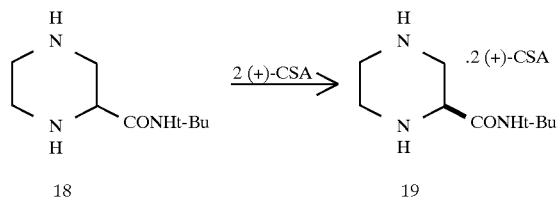

Materials

| rac-2-tert-Butyl-carboxamide-piperazine 18 in 1-Propanol Solution | 4.10 kg (22.12 mol) in 25.5 Kg solvent |
|---|---|
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 18 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 18 was 341 g/L. The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 18:2.5 min.

Acetonitrile (39 L) and water (2.4 L) were added to give a clear, slightly brown solution.

Determination of the water content by KF titration and $CH_3CN$/1-propanol ratio by $^1$H NMR integration showed that the $CH_3CN$/1-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN$/1-propanol/$H_2O$ 26/8/1.6 solvent mixture. It was dried at 35° C. in the vacuum oven with $N_2$ bleed to give 5.6 Kg (39%) of 19 as a white crystalline solid m.p. 288°–290° C. (with decomp.) $[\alpha]_D^{25}$= 18.9° (c=0.37, $H_2O$). $^{13}$C NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 19 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 14
(S)-2-tert-Butylcarboxamide-4-tert-butoxycarbonyl-piperazine 12 from salt 19

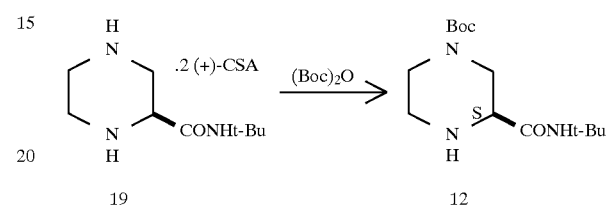

Materials

| (S)-2-tert-Butyl-carboxamide-piperazine Bis(S)-(+)-CSA salt 19, 95% ee | 5.54 Kg (8.53 mol) |
|---|---|
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 19 in a 100 L 3-neck flask with an addition funnel under $N_2$ was added EtOH, followed by triethylamine at 25 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time of 12=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 12 as a slightly tan powder. $[\alpha]_D^{25}=22.00$ (c=0.20, MeOH), m.p. 107° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 15

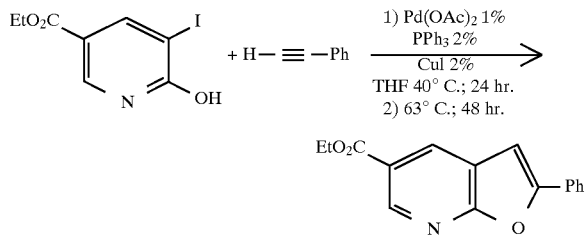

In a flame dried, 50 ml round bottom flask, iodide 2b (6.82 mmol) was added followed by Pd $(OAc)_2$ (0.0682 mmol), triphenyl-phosphine (0.137 mmol), and CuI (0.137 mmol). All solids were added in succession and, under slight $N_2$ pressure, were suspended in THF (11.0 mL). Phenylacetylene (7.64 mmol) and n-BuNH$_2$ (13.7 mmol) were added to give a green homogenous solution. The reaction mixture was then sealed under $N_2$ pressure and heated at +40° C. for 22–24 hrs where consumption of ethyl ester starting material and formation of the acetylene adduct was observed. The reaction mixture was then heated to +63° C. for 44–48 hrs where the acetylene adduct converted to the desired furopyridine. The reaction mixture was then partitioned between methylene chloride (50 ml) and disodium EDTA (5% aq. solution, 50 ml). The organic extract was then washed with sodium bisulfite (10% aq. solution, 50 mL), followed by 0.1N HCl (50 mL) and saturated aq. NaHCO$_3$ solution (50 mL). The organic extract was then dried over MgSO$_4$, filtered, and concentrated in vacuo. The crude material was then flashed chromatographed on SiO$_2$ using 12:1 hexanes-EtOAc to afford the desired product in 78% isolated yield.

EXAMPLE 16

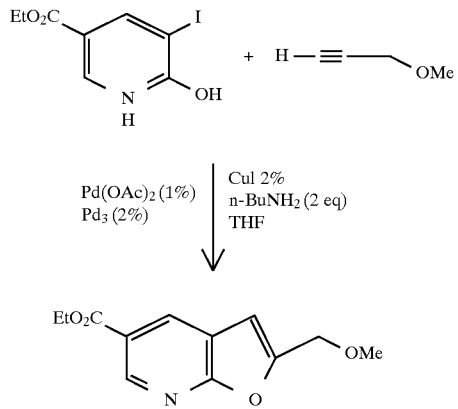

The iodide (1.76 g, 6 mmole), Pd(OAc)$_2$ (13.5 mg, 0.06 mmole), PPh$_3$ (31.5 mg, 0.1 mmole), CuI (22.9 mg, 0.12 mmole) were added as solids in a round-bottom flask under $N_2$ followed by n-BuNH$_2$ (1.2 mL, 12.0 mmole) and propanyl methyl ether (0.56 mL, 6.6 mmole) to give a green homogenous solution which was heated to 45°–50° C. for 48 hours. When HPLC analysis indicated no starting material was present, the mixture was partitioned between CH$_2$Cl$_2$ and disodium EDTA (5% aqueous solution) and the organic layer was washed in sequence with aqueous sodium bisulfite, 0.5N HCl and NaHCO$_3$ (aq). The organic layer was dried over MgSO$_4$, filtered and concentrated in vacuo and then chromatographed (flush-grade SiO$_2$, 3:1 hexanes-EtoAc) to give 1.07 g of product (76%).

EXAMPLE 17

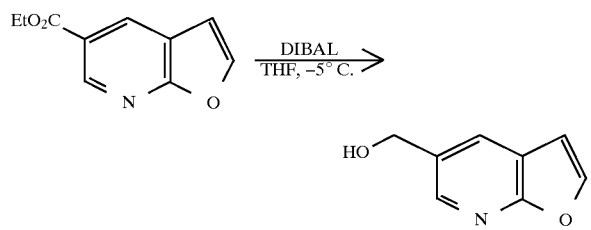

The ester (547.6 g, 2.87 mole) was dissolved in 12.9 Lt of dry THF and cooled to –7° C. and treated with 1.11 Lt of neat diisobutyl aluminum hydride (DIBAL) so that the temperature does not exceed –5° to –6° C. When tlc indicated complete consumption of starting material (ca 35 min) add saturated Na, K tartrate [10 kg of Na, K tartrat in 20 Lt of H$_2$O] so that the temperature remained below –4° C., (ca 8 Lt of "salt" solution added). Stop cooling, heat the mixture to 40° C. to ensure degassing of the mixture for 2 hours. Separate layers, add 12 Lt of isopropyl acetate and wash with additional 2 Lt of Na, K tartrate, separate layers and wash organic with 2 Lt of H$_2$O. Dry organic over MgSO$_4$, filter and recrystallize from Hexanes-1 PAC to give 780.3 g of alcohol.

EXAMPLE 18

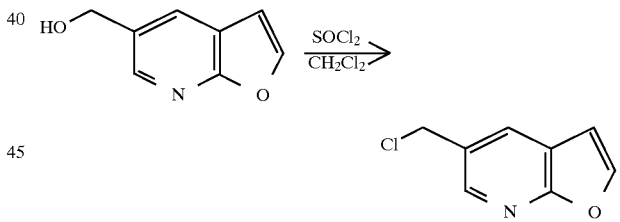

The alcohol (780 g, 4.81 mole, corrected for purity) was dissolved in 16 Lt of CH$_2$Cl$_2$ and the solution cooled to –2° C. SOCl$_2$ was added over 15 min so that the temperature did not exceed 0° C. The solution was warmed up to 15° C. for 2 hours at which point HPLC assay showed no starting material remaining. Slow addition of 16 Lt of NaHCO$_3$ (aqueous) produced a biphosic mixture. The organic layer was separated and treated with 40 g activated carbon (Darco G-60) and 1 kg of anhydrous Na$_2$SO$_4$, filtered and concentrated in vacuo to give 850.7 g of the desired chloride.

EXAMPLE 19
Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process of separating (1S,2R) indanyl epoxide in substantially 100% enantiomeric excess from a mixture comprising (1R,2S) indanyl epoxide and (1S,2R) indanyl epoxide, comprising the steps of
    (a) providing a mixture comprising (1R,2S) indanyl epoxide and (1S,2R) indanyl epoxide in buffer;
    (b) incubating the mixture with a suspension of fungal cells selected from the group consisting of *Diplodia gossipina* and *Lasiodiplodia theobromae* until substantially all of the (1R, 2S) indanyl epoxide is consumed; and
    (c) isolating the resulting (1S,2R) indanyl epoxide.

2. The process of claim 1, wherein the fungal cells are derived from ATCC 16391 or from ATCC 10936.

3. The process of claim 1, wherein said buffer is about 0.1M Tris, pH about 7.5, containing about 10% acetonitrile.

4. A process of purifying (1S,2R) indanyl epoxide in substantially 100% enantiomeric excess from a mixture comprising (1R,2S) indanyl epoxide and (1S,2R) indanyl epoxide, comprising the steps of
    (a) providing a mixture comprising (1R,2S) indanyl epoxide and (1S,2R) indanyl epoxide, at a concentration of about 1 g/L of said mixture in about 0.1M Tris, pH about 7.5, containing about 10% acetonitrile;
    (b) incubating the mixture with a suspension of fungal cells derived from *Diplodia gossipina* ATCC 16391, until substantially all of the (1R, 2S) indanyl epoxide is consumed; and
    (c) isolating the resulting (1S,2R) indanyl epoxide.

5. A process of purifying (1S,2R) indanyl epoxide in substantially 100% enantiomeric excess from a mixture comprising (1R,2S) indanyl epoxide and (1S,2R) indanyl epoxide, comprising the steps of
    (a) providing a mixture comprising (1R,2S) indanyl epoxide and (1S,2R) indanyl epoxide, at a concentration of about 1 g/L of said mixture in about 0.1M Tris, pH about 7.5, containing about 10% acetonitrile;
    (b) incubating the mixture with a suspension of fungal cells derived from *Diplodia gossipina* ATCC 10936, until substantially all of the (1R, 2S) indanyl epoxide is consumed; and
    (c) isolating the resulting (1S,2R) indanyl epoxide.

* * * * *